(12) United States Patent
Bodner

(10) Patent No.: US 11,951,020 B2
(45) Date of Patent: Apr. 9, 2024

(54) METHODS AND SYSTEMS FOR TARGETED ALIGNMENT AND SAGITTAL PLANE POSITIONING FOR HIP REPLACEMENT SURGERY

(71) Applicant: Russell J. Bodner, Maple Park, IL (US)

(72) Inventor: Russell J. Bodner, Maple Park, IL (US)

( * ) Notice: Subject to any disclaimer, the term of this patent is extended or adjusted under 35 U.S.C. 154(b) by 889 days.

(21) Appl. No.: 17/011,976

(22) Filed: Sep. 3, 2020

(65) Prior Publication Data

US 2021/0059838 A1    Mar. 4, 2021

Related U.S. Application Data

(60) Provisional application No. 62/895,085, filed on Sep. 3, 2019.

(51) Int. Cl.
*A61F 2/46* (2006.01)
*A61B 34/10* (2016.01)
(Continued)

(52) U.S. Cl.
CPC .......... *A61F 2/4609* (2013.01); *A61B 34/10* (2016.02); *A61F 2/4607* (2013.01); *G16H 20/40* (2018.01); *G16H 40/20* (2018.01); *G16H 40/40* (2018.01); *G16H 40/63* (2018.01); *G16H 50/30* (2018.01); *G16H 50/50* (2018.01); *G16H 50/70* (2018.01); *G16H 70/60* (2018.01); *A61B 2034/108* (2016.02); *A61B 34/20* (2016.02); *A61F 2002/4632* (2013.01);
(Continued)

(58) Field of Classification Search
CPC ............................. A61F 2/4609; A61B 34/10
See application file for complete search history.

(56) References Cited

U.S. PATENT DOCUMENTS

2010/0261998 A1   10/2010   Stiehl
2015/0088146 A1    3/2015   McCarthy
(Continued)

FOREIGN PATENT DOCUMENTS

WO    2019068194 A1    4/2019

OTHER PUBLICATIONS

PCT/US2020/049275, International Search Report dated Feb. 12, 2021.
(Continued)

*Primary Examiner* — Andrew Yang
(74) *Attorney, Agent, or Firm* — GrowIP Law Group LLC

(57) ABSTRACT

The disclosure provides example methods and non-transitory computer-readable mediums for acetabular cup placement. An example method includes a processor (a) determining for a first patient a sagittal acetabular cup position in the form of a standing AI, a seated AI and a SAA based on (i) a standing SS relative to a normative SS, (ii) a dSS between a standing position and an upright seated position, (iii) a femoral version corresponding to a femoral version outlier position, and (iv) a PFA to correspond to a PFA outlier position in a standing position or an upright seated position, (b) determining a coronal acetabular cup position in the form of a supine coronal anteversion and at least one of a supine or a standing coronal inclination based on the sagittal acetabular cup position, and (c) determining a post-operative standing AI and a post-operative seated AI based on the coronal acetabular cup position.

20 Claims, 9 Drawing Sheets

(51) Int. Cl.
*G16H 20/40* (2018.01)
*G16H 40/20* (2018.01)
*G16H 40/40* (2018.01)
*G16H 40/63* (2018.01)
*G16H 50/30* (2018.01)
*G16H 50/50* (2018.01)
*G16H 50/70* (2018.01)
*G16H 70/60* (2018.01)
*A61B 34/20* (2016.01)

(52) U.S. Cl.
CPC ............... *A61F 2002/4633* (2013.01); *A61F 2002/4668* (2013.01); *A61F 2002/4688* (2013.01); *A61F 2002/4689* (2013.01); *G05B 2219/45119* (2013.01)

(56) References Cited

U.S. PATENT DOCUMENTS

2016/0242934 A1  8/2016  Walt et al.
2017/0172697 A1  6/2017  Aghazadeh
2018/0235762 A1  8/2018  Radermacher et al.
2018/0318017 A1  11/2018  Fanson et al.

OTHER PUBLICATIONS

Stefl et al., "Spinopelvic mobility and acetabular component position for total hip arthroplasty", The Bone and Joint Journal, vol. 99-B, No. 1, 37-45 Jan. 2017.

```
                                    ┌─ 300
         ┌─ 305
┌────────────────────────────────────────────────────────┐
│ Determining, via a processor, a sagittal acetabular cup position in │
│   the form of a standing Anteinclination (AI), a seated AI and a    │
│ SacroAcetabular Angle (SAA) based on at least one of (i) a standing │
│   sacral slope (SS) of a first patient relative to a normative SS, (ii) a │
│  delta of the sacral slope (dSS) of the first patient between a standing │
│  position of the first patient and an upright seated position of the first │
│    patient, (iii) a femoral version of the first patient, when the femoral │
│   version corresponds to a femoral version outlier position, and (iv) a │
│   pelvic femoral angle (PFA) of the first patient that corresponds to a │
│  PFA outlier position in at least one of a standing position, an upright │
│   seated position, or a delta between the standing position and the │
│                     upright seated position                         │
└────────────────────────────────────────────────────────┘
         ┌─ 310               ↓
┌────────────────────────────────────────────────────────┐
│ Determining, via the processor, a coronal acetabular cup position in │
│   the form of a supine coronal anteversion and at least one of a    │
│       supine or a standing coronal inclination based on the sagittal │
│                   acetabular cup position                           │
└────────────────────────────────────────────────────────┘
         ┌─ 315               ↓
┌────────────────────────────────────────────────────────┐
│ Determining, via a processor, a post-operative standing AI and a    │
│  post-operative seated AI based on at least the coronal acetabular  │
│                        cup position                                 │
└────────────────────────────────────────────────────────┘
```

FIG. 12

CORONAL SUPINE COORDINATES: PI & SS Norms vs dSS
RAPIOGRAPHIC INCLINATION & ANTEVERSION
SAA
AI Standing & AI Sitting

| SS | PI | 5 | 10 | 15 | 20 | 25 | 30 | 35 | 40 |
|---|---|---|---|---|---|---|---|---|---|
| 58.33 | 80 | 44/28<br>9.5<br>37/42 | 42/27<br>92.5<br>34.5/44.5 | 40/25<br>90<br>32/47 | 37/23.5<br>87.5<br>29.5/49.5 | 36/22<br>85<br>27/52 | 35.5/20<br>87.5<br>24.5/54.5 | 35/19<br>80<br>22/57 | 35/17<br>77.5<br>19.5/59.5 |
| 51.67 | 70 | 44/27<br>90<br>38/43 | 43/26<br>87.5<br>35.5/45.5 | 41/24<br>85<br>33/48 | 38/22.5<br>82.5<br>30.5/50.5 | 37/21<br>80<br>28/53 | 36/19<br>77.5<br>25.5/55.5 | 35.5/18<br>75<br>23/58 | 33/15<br>72.5<br>20.5/60.5 |
| 45 | 60 | 45/26<br>85<br>40/45 | 44/24<br>82.5<br>37.5/47.5 | 42/22.5<br>80<br>35/50 | 39/21<br>77.5<br>32.5/52.5 | 38/19<br>75<br>30/55 | 37/18<br>72.5<br>27.5/57.5 | 36/17<br>70<br>25/60 | 36/14<br>67.5<br>22.5/62.5 |
| 38.33 | 50 | 46/24.5<br>80<br>42/47 | 44.5/23<br>77.5<br>39.5/49.5 | 42.5/21.5<br>75<br>37/52 | 40/20<br>72.5<br>34.5/54.5 | 39/18<br>70<br>32/57 | 38/17<br>67.5<br>29.5/59.5 | 37.5/16<br>65<br>27/62 | 37/13.5<br>62.5<br>24.5/64.5 |
| 31.67 | 40 | 47/23<br>75<br>43/48 | 47/22<br>72.5<br>40.5/50.5 | 43.5/20<br>70<br>38/53 | 42/18<br>67.5<br>35.5/53.5 | 41/17<br>65<br>33/58 | 40/15.5<br>62.5<br>30.5/60.5 | 39.5/14<br>60<br>28/63 | 39/12.5<br>57.5<br>25.5/65.5 |
| 25 | 30 | 48/22<br>70<br>45/50 | 46/21<br>67.5<br>42.5/52.5 | 45/19<br>65<br>40/55 | 44/17<br>62.5<br>37.5/57.5 | 43/15<br>60<br>35/60 | 42/14<br>57.5<br>32.5/62.5 | 41/13<br>55<br>30/65 | 40/12<br>52.5<br>27.5/67.5 | dSS

FIG. 13

METHODS AND SYSTEMS FOR TARGETED ALIGNMENT AND SAGITTAL PLANE POSITIONING FOR HIP REPLACEMENT SURGERY

CROSS-REFERENCE TO RELATED APPLICATIONS

This application claims the benefit of the filing date of U.S. Provisional Patent Application No. 62/895,085, filed on Sep. 3, 2019, which is hereby incorporated by reference in its entirety.

BACKGROUND

Historically, since 1978, the frontal or coronal plane has solely been utilized to plan and assess the spatial position of the acetabular component or cup of a hip replacement. Lewinnek et al described a 20×20 degree acceptable or "safe zone" measured on a single X-ray of a patient lying flat on an X-ray table with the beam shooting down onto the pelvis in the frontal plane. Two parameters were described, namely inclination and anteversion for this zone with 30-50 degrees and 5-25 degrees respectively as the acceptable range for surgeons to target the acetabular cups. Attempts were made to standardize the patient's position on the table by leveling the front of the pelvis with a true mechanical level and this plane was described as the Anterior Pelvic Plane (APP). APP was observed to not be the same in patients and that when the APP deviated from 0 degrees APP could affect the position of the cup. The Lewinnek safe zone has been adopted as the gold standard for cup placement ever since, even though actual attempts to try to level the pelvis are rare if non-existent.

In about 1999, research surgeons began trying to capture the deviation of the APP in order to correct the acetabular cup intraoperatively back to a neutral position. This process spawned development of the first computer assisted hip surgery and was call "tilt adjustment". At present, only a small number of surgeons use a tilt adjustment or computers. Tilt adjustment surgeries have not been found to lower the complication of the acetabular cups dislocating, as this adjustment is a static adjustment in the supine position of the APP to the neutral position.

Approximately 15 years ago Lazennec began studying the functional motions of the spine-pelvis-hip complex with regards to hip replacement surgery, using terminology developed in the field of spinal surgery and defined a new paradigm for assessment of the acetabular cup in the sagittal plane. He used lateral images from a new low dose X-ray scanner called the EOS Imaging System (Paris, France) and measured the acetabular cup's position and behavior in different functional positions (i.e., standing upright and sitting upright inside the scanner). The lateral or sagittal plane measurement of the cup in space was defined and has come to be known as Anteinclination (AI) through the works of Don. In addition, a new constant measure relating this acetabular cup position to the position of the pelvis was created, and named the Sacroacetabular Angle (SAA) by Lazennec.

Lazennec did not develop his findings into a methodology to target components. Instead, Don used coronal targeting research to amass data on these sagittal plane parameters and publish ranges and means for AI and SAA. Dorr also characterized the aberrations of pelvic position and pelvic mobility that created the outlier pelvic behavior causing the mechanical risks for implant failure.

SUMMARY

The present disclosure leverages biomechanical properties of the spino-pelvic-femoral complex and provides methods for planning (including use of digital platforms), tracking, targeting, navigation, and placement (including assisted or robotic execution) in vivo of the acetabular cup of a total hip replacement (i.e., total hip arthroplasty). Specifically, methods are provided that permit an acetabular cup to be individually targeted based on sagittal parameters. These sagittal parameters link the cup to the pelvis with respect to both the tilt (i.e., pelvic position) and the mobility (i.e., pelvic excursion) thereby producing optimal Anteinclination (AI) and Sacroacetabular Angle (SAA) values. These goniometric ratios permit the methods of the present disclosure to track the acetabular cup in space and to execute the acetabular position with an individual target based on a patient's measurements with increased accuracy over the 20×20° Lewinnek zone. These methods of the present disclosure may be used to analyze preoperative studies, including X-rays, CT scans, and MRI scans to determine a recommended orientation of the acetabular cup on patient-by-patient basis. The methods of the present disclosure may also be used to provide intraoperative guidance as to the position of the implant by tracking anatomy and the implant in space and automating, in whole or in part, navigation equipment to place the acetabular cup.

In one aspect, an example method is disclosed. The method includes (a) determining, via a processor, a sagittal acetabular cup position in the form of a standing Anteinclination (AI), a seated AI and a SacroAcetabular Angle (SAA) based on at least one of (i) a standing sacral slope (SS) of a first patient relative to a normative SS, (ii) a delta of the sacral slope (dSS) of the first patient between a standing position of the first patient and an upright seated position of the first patient, (iii) a femoral version of the first patient, when the femoral version corresponds to a femoral version outlier position, and (iv) a pelvic femoral angle (PFA) of the first patient that corresponds to a PFA outlier position in at least one of the standing position, the upright seated position, or a delta between the standing position and the upright seated position, (b) determining, via the processor, a coronal acetabular cup position in the form of a supine coronal anteversion and at least one of a supine or a standing coronal inclination based on the sagittal acetabular cup position, and (c) determining, via a processor, a post-operative standing AI and a post-operative seated AI based on at least the coronal acetabular cup position.

In another aspect, an example non-transitory computer-readable medium is disclosed. The computer readable medium has stored thereon program instructions that upon execution by a processor, cause performance of a method including (a) the processor determining a sagittal acetabular cup position in the form of a standing Anteinclination (AI), a seated AI and a SacroAcetabular Angle (SAA) based on at least one of (i) a standing sacral slope (SS) of a first patient relative to a normative SS, (ii) a delta of the sacral slope (dSS) of the first patient between a standing position of the first patient and an upright seated position of the first patient, (iii) a femoral version of the first patient, when the femoral version corresponds to a femoral version outlier position, and (iv) a pelvic femoral angle (PFA) of the first patient that corresponds to a PFA outlier position in at least one of the standing position, the upright seated position, or a delta between the standing position and the upright seated position, (b) the processor determining a coronal acetabular cup position in the form of a supine coronal anteversion and at least one of a supine or a standing coronal inclination based on the sagittal acetabular cup position, (c) and the processor determining a post-operative standing AI and a post-operative seated AI based on at least the coronal acetabular cup position.

The features, functions, and advantages that have been discussed can be achieved independently in various examples or may be combined in yet other examples further details of which can be seen with reference to the following description and drawings.

BRIEF DESCRIPTION OF THE DRAWINGS

FIG. 12 shows a flowchart of a method, according to an example implementation.

FIG. 13 shows a table of radiographic inclination and anteversion SAA and standing and sitting AI determined using the methods of the present disclosure.

Figure 1:
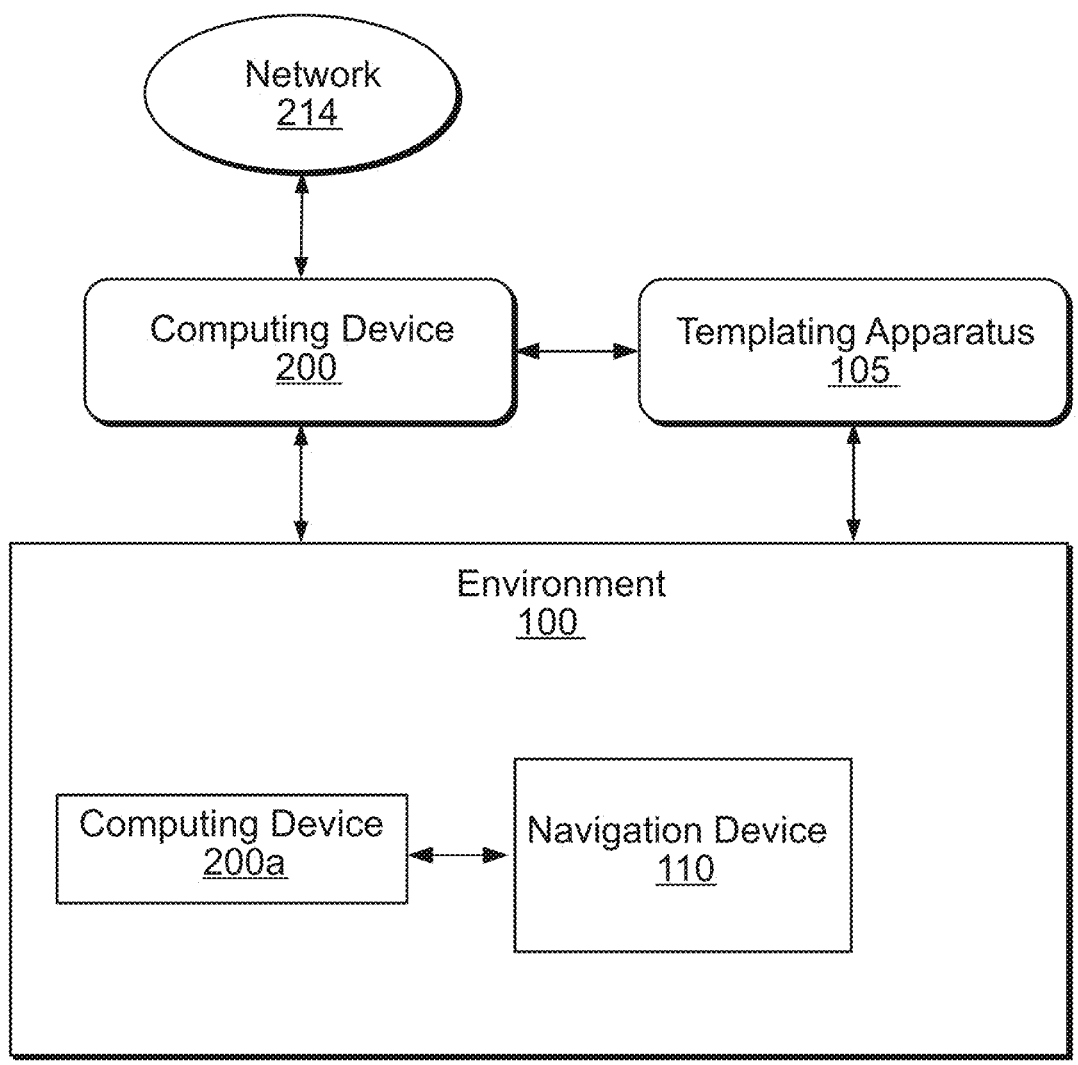
FIG. 1 is a functional block diagram of a system, according to one example implementation.

The drawings are for the purpose of illustrating examples, but it is understood that the inventions are not limited to the arrangements and instrumentalities shown in the drawings.

DETAILED DESCRIPTION

As used herein, "Anterior Pelvic Plane" ("APP") refers to the plane traditionally used to measure or normalize (level) the sagittal tilt of the pelvis with respect to the coronal (longitudinal) plane of the body. The APP is the plane defined by three points, the right and left Anterior Superior Iliac Spines and the pubis symphysis prominence.

As used herein, "Anteinclination" ("AI") or Sagittal Angle of Inclination ("SAT") refers to the lateral or sagittal plane measurement of the acetabular cup in space. AI consists of a line tangent to the face of the sagittal projection of the acetabular implant and the horizontal reference line (i.e., parallel to the ground). The conventional limits of this parameter range from 25-45 degrees in a standing position and ranges from 45-65 degrees in a seated position. The present disclosure contemplates an AI or SAI ranging from 23-50 degrees in the standing position and ranges from 45-70 degrees in the seated position. AI of the acetabular component is a 2-dimensional measure based on a lateral X-ray film. AI represents the operative or sagittal plane anteversion of the acetabular cup (i.e., the angle between the longitudinal axis of the patient and the acetabular component axis as projected onto the sagittal plane), with a minor influence of operative inclination. In other words, AI is a direct measure of anteversion, but the AI value is a different number from the coronal plane value used by surgeons. The anteversion clinically used by surgeons is called the radiographic anteversion, which is the projection of anteversion measured on an anterior to posterior (AP) X-ray as the patient is lying supine on a table.

As used herein, "Sacral Slope" ("SS") refers to the angle between the horizontal reference line and the tangent line along the sacral promontory (also referred to as the sacral endplate) having normal standing ranges from 20°-57°, sitting from 5°-35° for Pelvic Incidence values between 25°-80°.

As used herein, "dSS," when applied to the SS value, refers to a delta or numerical change when moving a pelvis and an implanted acetabular cup between two positions. The measurements are obtained when the pelvic sacral slope angle is measured in two positions, namely the standing position and the upright seated position.

As used herein, "SacroAcetabular Angle" ("SAA") refers to a constant measure relating the AI cup position to the position of the pelvis. The SAA is formed by the anterior extension of the line tangent to the sacral promontory and the anterior extension of the line tangent to the sagittal face of the acetabular cup (i.e., AI+SS). When dSS is 25 degrees, SAA is also equal to (90+PI)/2.

As used herein, "Pelvic Tilt" ("PT") refers to a positional parameter formed by the angle between the vertical reference line and a line connecting the center of the bicoxofemoral axis and the center of the S1 promontory.

As used herein, "Pelvic Mobility" refers to pelvic excursion and is synonymous with dSS.

As used herein, "Pelvic Incidence" ("PI") refers to a morphologic constant parameter in the sagittal plane that categorizes pelvic construction, PI is equal to the sum of the Pelvic Tilt and Sacral Slope angles (i.e., PT+SS). PI is formed by the line connecting the center of the bicoxofemoral axis and the center of the S1 promontory and a second line perpendicular to the S promontory at the S1 promontory's central point. The typical human range is 25-80 degrees with a mean of 52-53, values under 30 and above 75 are rare.

As used herein, Pelvic Acetabular Angle ("PAA") refers to an angle that corresponds to (90-AI)+PT. This angle was first described, defined, and leveraged in the disclosed methods by Dr. Bodner, the inventor.

As used herein, "Bodner's Triangle" refers to a triangle that has three angles, namely (i) the SAA, (ii) (90-PI) at the sacral apex, and (iii) the PAA. The three sides are formed by the extension of the SS line anteriorly and inferiorly intersecting with the extension of the AI line superiorly and anteriorly, with the third side the PT line connecting the hip center to the center of the S1 endplate. Therefore, the geometric construct of Bodner's Triangle ties together the acetabular cup's spatial position to that of the pelvic construction and spatial position. Bodner's triangle is influenced in form, spatial orientation, and excursion by all by each angle that it comprises, namely PI, SS, PT, AI, and functionally by the excursion or mobility between positions that is defined as dSS.

As used herein, "electrically coupled" refers to coupling using a conductor, such as a wire or a conductible trace, as well as inductive, magnetic and wireless couplings.

As used herein, "sagittal feedback" includes biomechanical values such the pelvic incidence (PI), the sacral slope (SS), the pelvic tilt (PT), the delta (dSS) of the sacral slope (SS), the pelvic femoral angle (PFA), the leg length, a hip offset, a hip center of rotation, and a femoral version.

Overview

Embodiments of the preoperative templating apparatus, navigation devices and methods described herein can be used to determine a spatial position and orientation of the acetabular component and provide intraoperative guidance or control as to the spatial position and orientation of the acetabular component by tracking patient anatomy and the acetabular component in real-time. The disclosed example preoperative templating apparatus, navigation devices and methods also beneficially obtain and provide on a display sagittal feedback detailing or illustrating the acetabular component's position and may also be used to determine a coronal position based on the obtained sagittal feedback consisting of the AI, SAA, all obtainable from the SS measured in the standing and sitting positions.

Example Architecture

FIG. 1 is a block diagram showing an operating environment 100 that includes or involves, for example, preoperative templating apparatus 105 or navigation device 110. Method 300 in FIG. 10 described below shows an embodiment of a method that can be implemented within this operating environment 100.

Figure 2:
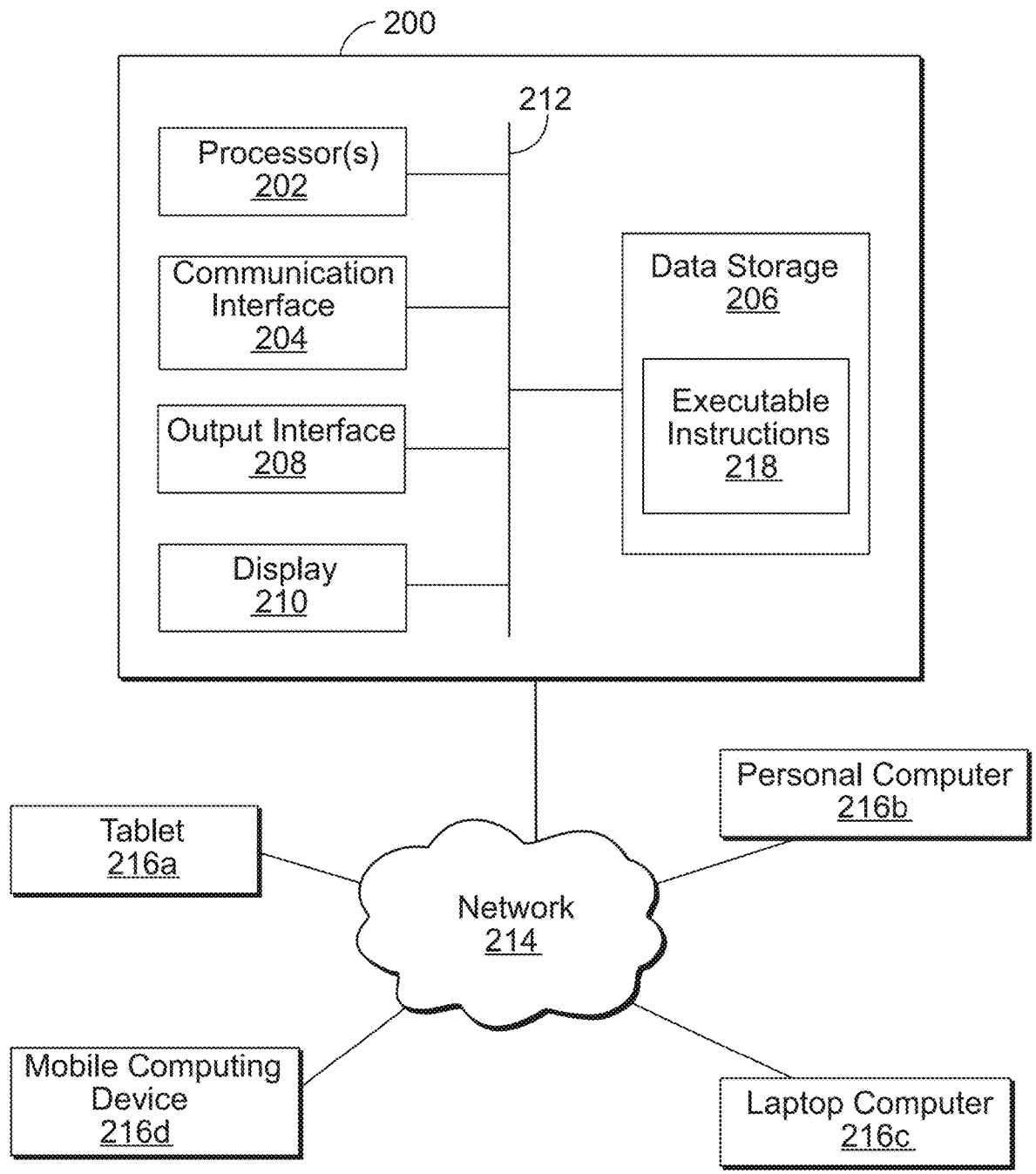
FIG. 2 depicts a block diagram of a computing device and a computer network, according to an example implementation.

FIG. 2 is a block diagram illustrating an example of a computing device 200, according to an example implementation, that is configured to interface with operating environment 100, either directly or indirectly. The computing device 200 may be used to perform functions of the method shown in FIG. 10 and described below. In particular, computing device 200 can be configured to perform one or more functions, including determining a spatial position and orientation of the acetabular component and providing intraoperative guidance or control as to the spatial position and orientation of the acetabular component by tracking patient anatomy and the acetabular component in real-time, for example, as well as, obtaining and providing on a display sagittal feedback detailing or illustrating the acetabular component's position and determining a coronal position based on the obtained sagittal feedback. The computing device 200 has a processor(s) 202, and also a communication interface 204, data storage 206, an output interface 208, and a display 210 each connected to a communication bus 212. The computing device 200 may also include hardware to enable communication within the computing device 200 and between the computing device 200 and other devices (e.g. not shown). The hardware may include transmitters, receivers, and antennas, for example.

The communication interface 204 may be a wireless interface and/or one or more wired interfaces that allow for both short-range communication and long-range communication to one or more networks 214 or to one or more remote computing devices 216 (e.g., a tablet 216a, a personal computer 216b, a laptop computer 216c and a mobile computing device 216d, for example). Such wireless interfaces may provide for communication under one or more wireless communication protocols, such as Bluetooth, WiFi (e.g., an institute of electrical and electronic engineers (IEEE) 802.11 protocol), Long-Term Evolution (LTE), cellular communications, near-field communication (NFC), and/or other wireless communication protocols. Such wired interfaces may include Ethernet interface, a Universal Serial Bus (USB) interface, or similar interface to communicate via a wire, a twisted pair of wires, a coaxial cable, an optical link, a fiber-optic link, or other physical connection to a wired network. Thus, the communication interface 204 may be configured to receive input data from one or more devices, and may also be configured to send output data to other devices.

The communication interface 204 may also include a user-input device, such as a keyboard, a keypad, a touch screen, a touch pad, a computer mouse, a track ball and/or other similar devices, for example.

The data storage 206 may include or take the form of one or more computer-readable storage media that can be read or accessed by the processor(s) 202. The computer-readable storage media can include volatile and/or non-volatile storage components, such as optical, magnetic, organic or other memory or disc storage, which can be integrated in whole or in part with the processor(s) 202. The data storage 206 is considered non-transitory computer readable media. In some examples, the data storage 206 can be implemented using a single physical device (e.g., one optical, magnetic, organic or other memory or disc storage unit), while in other examples, the data storage 206 can be implemented using two or more physical devices.

The data storage 206 thus is a non-transitory computer readable storage medium, and executable instructions 218 are stored thereon. The instructions 218 include computer executable code. When the instructions 218 are executed by the processor(s) 202, the processor(s) 202 are caused to perform functions. Such functions include, but are not limited to, determining a spatial position and orientation of the acetabular component and providing intraoperative guidance or control as to the spatial position and orientation of the acetabular component by tracking patient anatomy and the acetabular component in real-time, for example, as well as, obtaining and providing on a display sagittal feedback detailing or illustrating the acetabular component's position and determining a coronal position based on the obtained sagittal feedback.

The processor(s) 202 may be a general-purpose processor or a special purpose processor (e.g., digital signal processors, application specific integrated circuits, etc.). The processor(s) 202 may receive inputs from the communication interface 204, and process the inputs to generate outputs that are stored in the data storage 206 and output to the display 210. The processor(s) 202 can be configured to execute the executable instructions 218 (e.g., computer-readable program instructions) that are stored in the data storage 206 and are executable to provide the functionality of the computing device 200 described herein.

The output interface 208 outputs information to the display 210 or to other components as well. Thus, the output interface 208 may be similar to the communication interface 204 and can be a wireless interface (e.g., transmitter) or a wired interface as well. The output interface 208 may send commands to one or more controllable devices, for example The computing device 200 shown in FIG. 2 may also be representative of a local computing device 200a in operating environment 100, for example, in communication with rinse station apparatus 105. This local computing device 200a may perform one or more of the steps of the method 300 described below, may receive input from a user and/or may send image data and user input to computing device 200 to perform all or some of the steps of method 300. In addition, in one optional example embodiment, the preoperative templating apparatus or navigation device 105 may be utilized to perform method 300.

Figure 10:
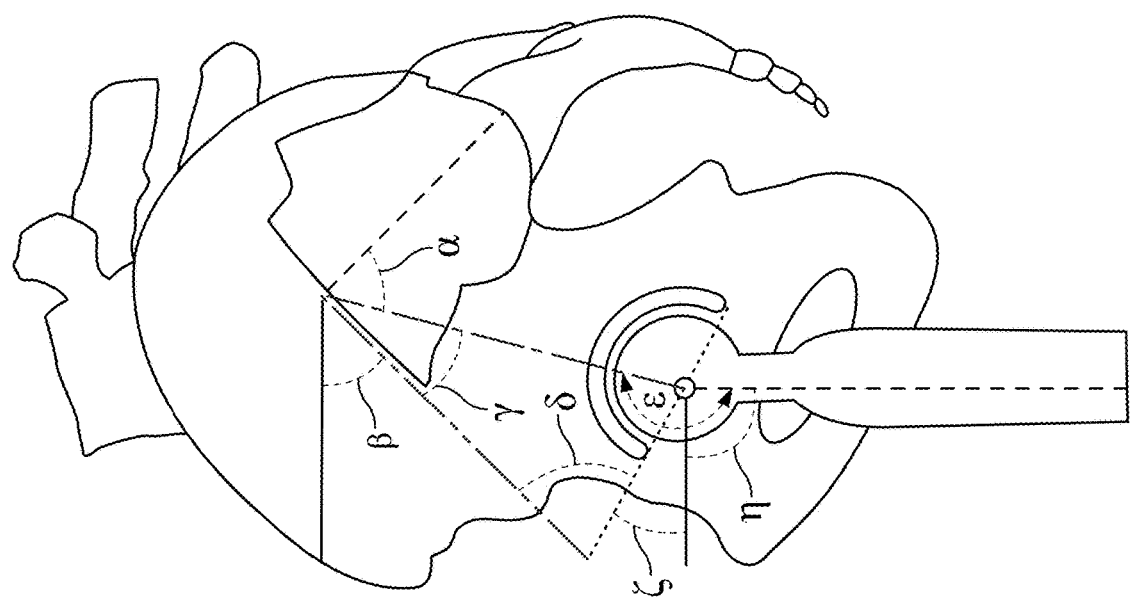
FIG. 10 shows a standing lateral view according to one example in which PI is 60° (α), SS is 45° (β), 90-PI is 30° (γ), SAA is 75° (δ), PAA is 75° (ε), AI is 30° (ζ), and PFA is 195° (η). Bodner's triangle is formed by angles (δ), (ε), and (γ). As shown, SAA links SS and the acetabulum (anteinclination AI). PAA connects the pelvic tilt (PT) to AI. And PFA links femoral motion to the pelvis.

Method 300 shown in FIG. 10 presents an example of a method that could be used with the computing device 200 of FIG. 2, for example. Further, devices or systems may be used or configured to perform logical functions presented in FIG. 10. In some instances, components of the devices and/or systems may be configured to perform the functions such that the components are configured and structured with hardware and/or software to enable such performance. Components of the devices and/or systems may be arranged to be adapted to, capable of, or suited for performing the functions, such as when operated in a specific manner. Method 300 may include one or more operations, functions, or actions as illustrated by one or more of blocks 305-315. Although the blocks are illustrated in a sequential order, some of these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of the present examples. In this regard, each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time such as register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block in FIG. 10, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

Overview of Methodology

In the sagittal plane there are two fundamental relationships between five parameters that link the acetabulum to the pelvic orientation. The first relationship is for the pelvic rotational changes inherent in the pelvis's construction, namely pelvic incidence (PI) corresponds to pelvic tilt (PT) in combination with sacral slope (SS). The second relationship is between the acetabular cup and the pelvis as they both rotate in space such that sacroacetabular angle (SAA) corresponds to anteinclination (AI) in combination with sacral slope (SS). PI and SAA are fixed constants over any position while PT, SS and AI are reciprocal parameters that change on a 1:1 ratio as the pelvis assumes different positions. PI and SAA share the SS parameter which allows the various parameters to be related to each other, for example, PI-PT=SAA-AI that expresses the pelvic parameters on the left and acetabular parameters on the right.

Figure 3B:
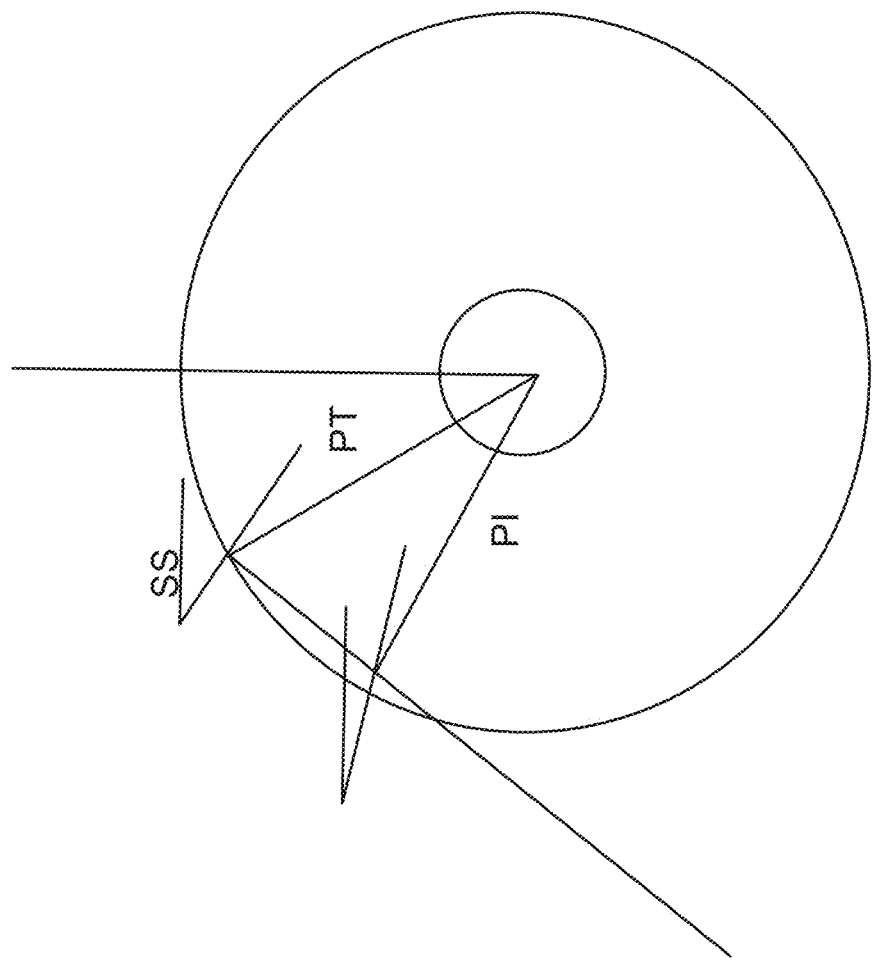
FIG. 3B is a schematic that shows the positional influence of pelvic incidence (PI) in the standing and seated positions. For example, High PI can be seen to move through a larger arc with greater change between sacral slope and pelvic tilt than in FIG. 3A, both the positional adaptability and lumbar spine changes will be greater. The angle for pelvic incidence is labeled "PI" and the angle for pelvic tilt is labeled PT, the bold lines along the outer circle represent the S1 promontory and the central circle represents the bicoxofemoral axis. The arc of rotation in FIGS. 3A-3B is determined by the normalized linear distance (i.e., the distance relative to the length of the sacral endplate that has been validated) between the center of the femoral heads and the sacral promontory centroid and is inversely dependent of the PI angle itself, here they are drawn as similar circles. The angular change between the two positions is the pelvic retroversion or delta SS. An acetabular implant will rotate through this exact same arc as it sits above the femoral head.
Figure 3A:
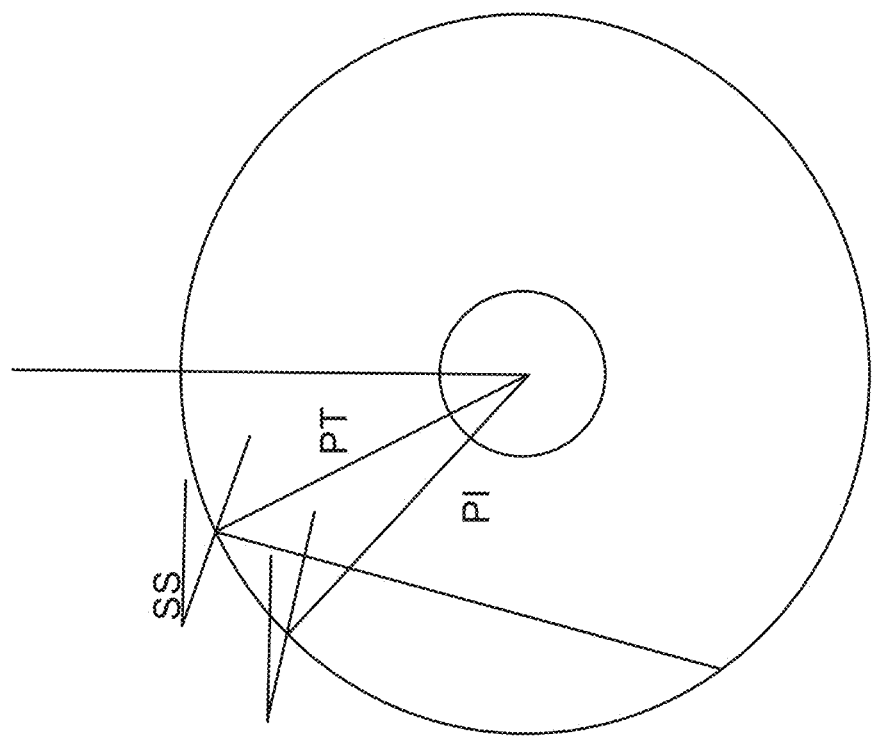
FIG. 3A is a schematic that shows the positional influence of pelvic incidence (PI) in the standing and seated positions. For example, a low PI describes a limited arc of posterior rotation around the bicoxofemoral axis as Sacral Slope (SS) decreases and pelvic tilt increases. Postural adaptability is gained through the increased horizontal distance behind the femoral heads as well as through the straightening or flexion of the lumbar spine. The angle for pelvic incidence is labeled "PI" and the angle for pelvic tilt is labeled PT, the bold lines along the outer circle represent the S1 promontory and the central circle represents the bicoxofemoral axis.
Figure 4:
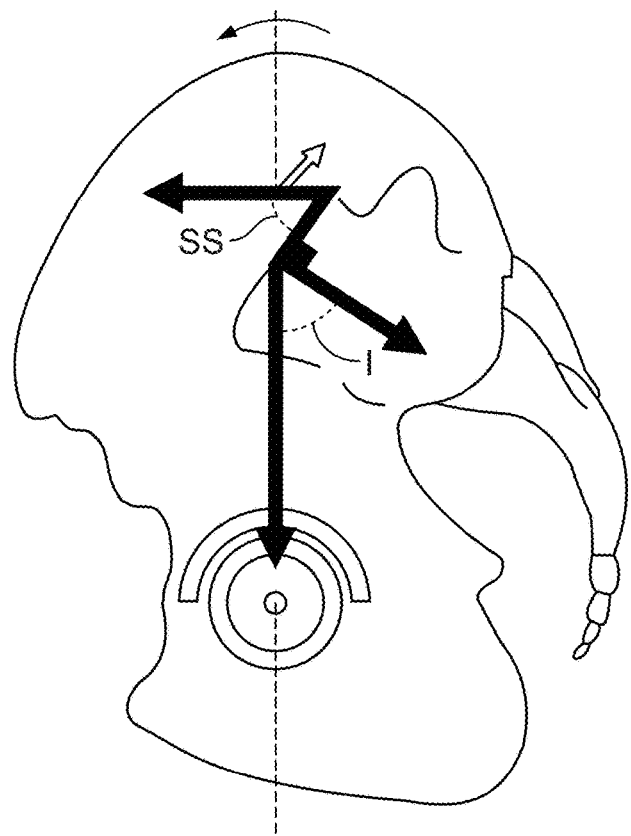
FIG. 4 shows a standing lateral view of the pelvis having a PT of 0°, which is rarely encountered.
Figure 5:
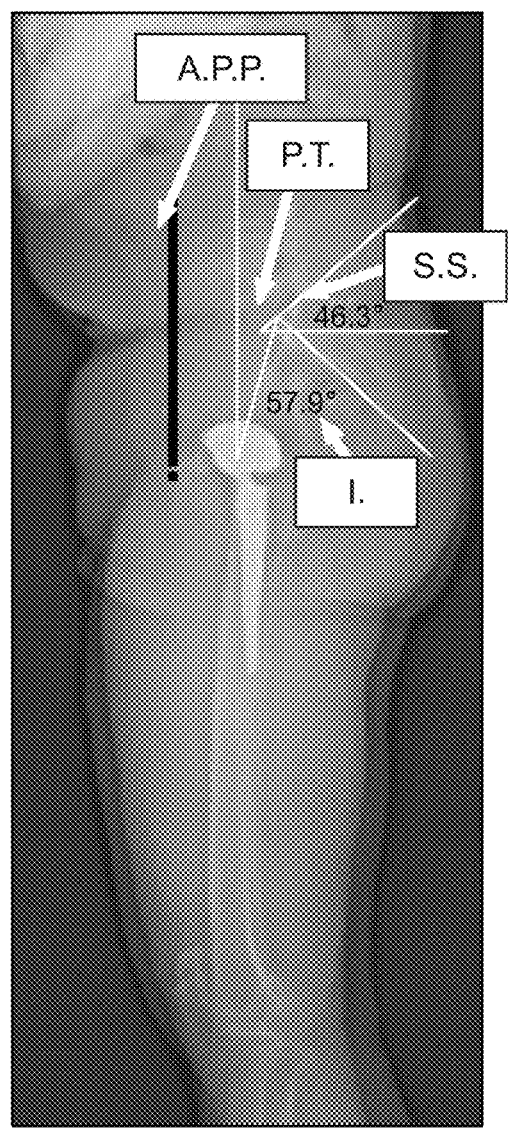
FIG. 5 shows an X-ray image of a standing lateral view that shows the pelvis rotated forward increasing the sacral slope (SS) at the expense of the pelvic tilt (PT). The X-ray depicts the finding of the Anterior Pelvic Plane, APP (defined below) of 0° standing, the sagittal parameters are normal, PI (I) is 58°, SS 44°, PT 14°. The unmeasured cup SAI is approximated between 25-30°.
Figure 7:
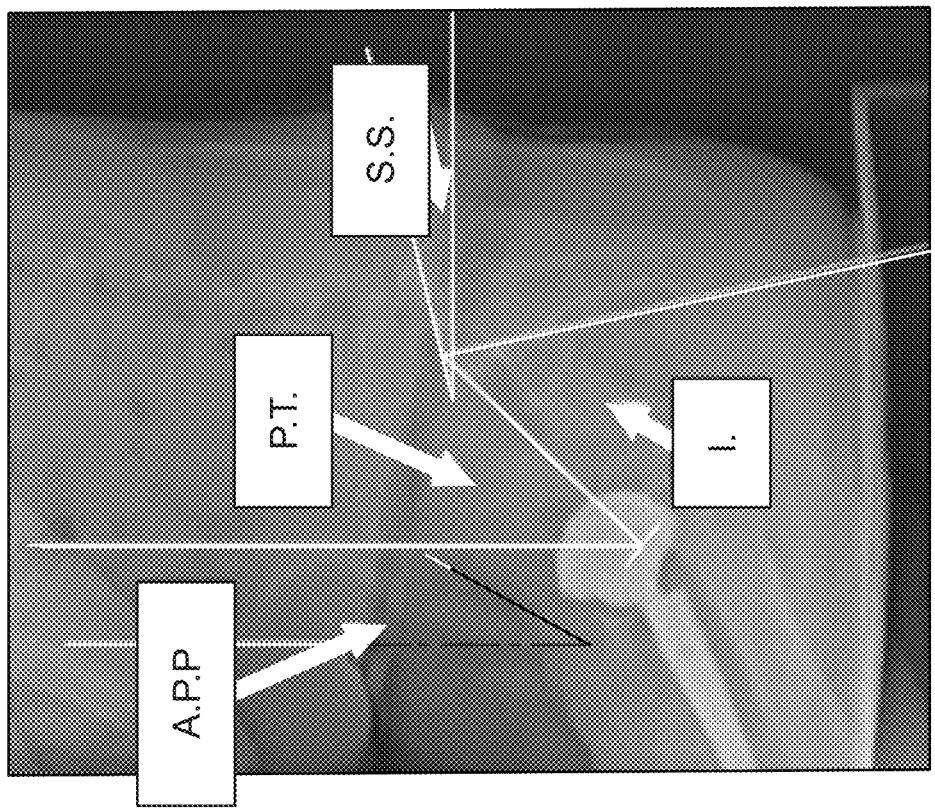
FIG. 7 shows an X-ray image of a seated lateral view of the pelvis showing equivalent angular increase of 27 degrees in APP, PT and the cup AI from the standing position of FIG. 5, the fixed parameters PI (I) and SAA (unmeasured) remain unchanged. The ample dynamic mobility of the pelvis and lumbar spine allows sitting with only 60 degrees of hip flexion, this makes anterior impingement and posterior instability risk negligible.
Figure 6:
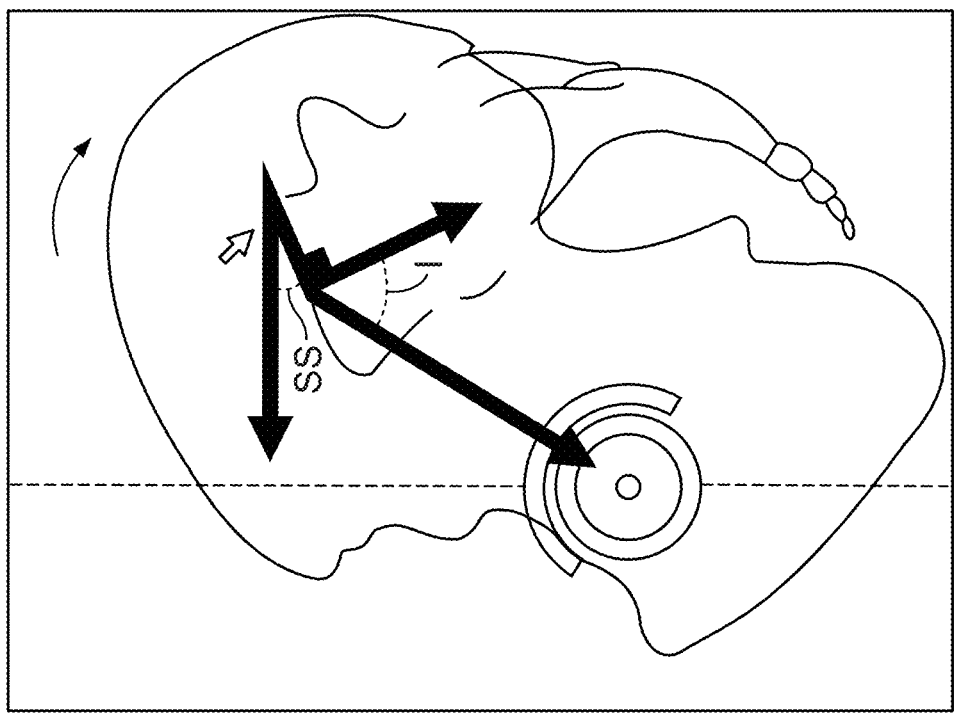
FIG. 6 shows a seated lateral view showing the posterior rotation of the pelvis around the axle connecting the femoral heads, the bicoxofemoral axis, this decreases the SS while reciprocally increasing PT.
Figure 9:
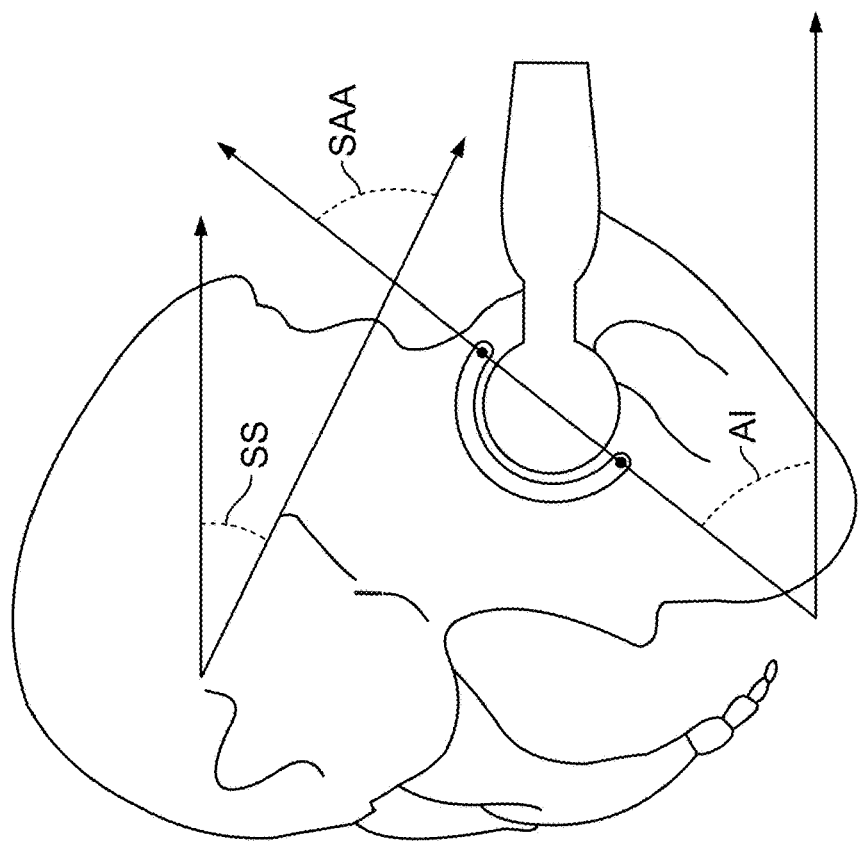
FIG. 9 shows a seated lateral view of the pelvis of FIG. 8.
Figure 8:
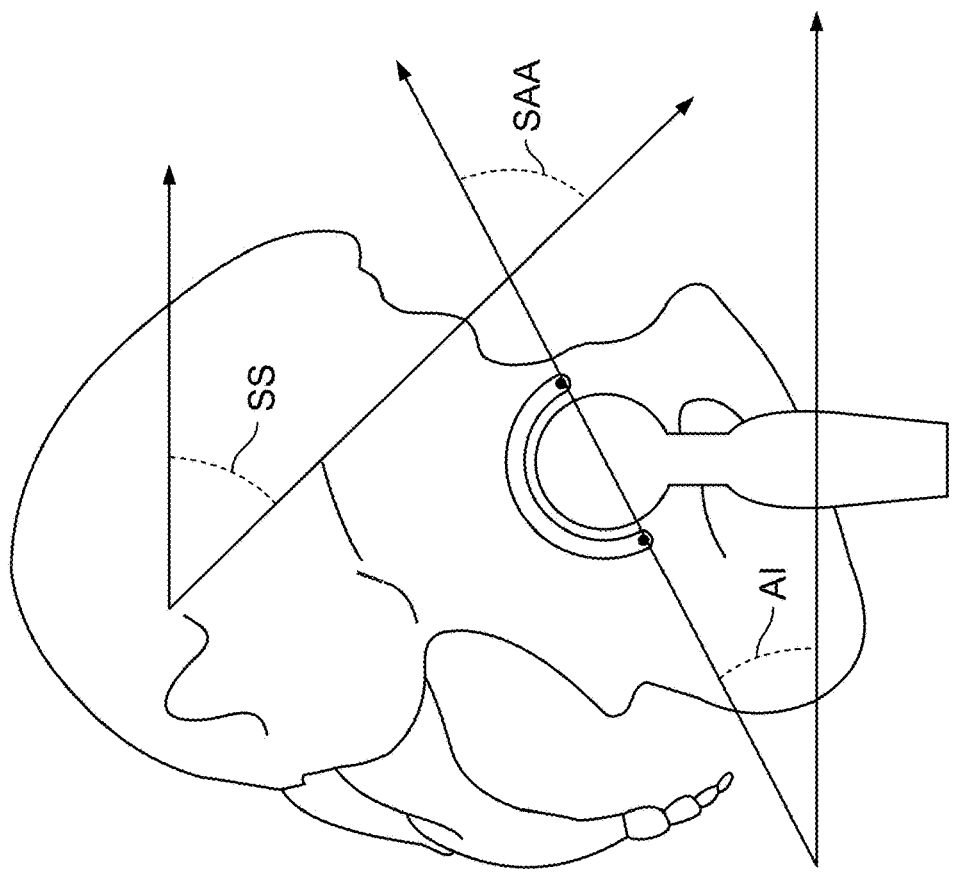
FIG. 8 shows a standing lateral view of the pelvis Sacroacetabular Angle SAA is formed by the line tangent to the sacral promontory and the line tangent to the sagittal face of the cup. This angle, created at surgery, is fixed and composed of the sum of the anteinclination (SI here) and sacral slope (SS), SAA=SI+SS. It defines the relationship of the cup to the pelvis with a range of 75+/−15 degrees as the normal. Creating a Sacroacetabular Angle SAA that is too high, influenced by pelvic retroversion and low PI as manifest in the stuck sitting imbalanced group, is associated with posterior impingement and anterior instability. Creating a Sacroacetabular Angle SAA that is too low, associated with high PI and seen with the stuck standing imbalanced group, is associated with anterior impingement and posterior instability.

Additionally, these equations are applicable when the parameters are measured in different functional positions, and may be applied to the data that exists for measures taken with the patient standing and seated prior to surgery. Spinal surgeons use the PI relationship to assist in correcting spinal deformities but this has only been applied to the standing position, and these parameters have not been managed over different positions. For example, moving a pelvis and acetabular cup between the two positions creates a delta or numerical change (dSS) when applied to the SS value. The pelvis and the acetabular cup move together as the acetabular cup is firmly fixed into the acetabulum, a part of the pelvis. The methods of the present disclosure contemplate superimposing the components of the PI and SAA relationships on a lateral rendering, as shown in FIG. 3, thereby illustrating new angular relationships not previously known or utilized.

The technical effect of the methods leveraging the ratios between these angular parameters is to determine the degree to which changes in one parameter affect another parameter and how different amounts of mobility affect the acetabular-cup related parameters. With respect to the pelvis, spine surgeons have described that as PI changes 10 degrees, SS changes approximately 6 degrees and PT 4 degrees. The present disclosure includes methods that determined a refined ratio, starting at PI of 15, SS of 15, and PT of 0 degrees, every 3-degree rise in the constant PI of the pelvis causes a 2 degree rise in the SS, and a 1 degree rise in the PT, that is, the inherent ratio between PI:SS:PT is 3:2:1. These unique geometric relationships are SS=5+0.666PI and PT=−5+0.333PI. Therefore a PI of 45 degrees in a normal individual will have a standing SS of 35 degrees, and a PT of 10 degrees; likewise, a PI of 60 degrees yields a standing SS of 45 degrees and a PT of 15 degrees. PT and SS values change from this normal relationship in people as they age and with disease but for every degree of change in SS, PT will change 1 degree in the opposite direction, in individuals these parameters are reciprocal.

Leveraging the effects of pelvic position and mobility in the methods of the present disclosure advantageously permit a determination of AI and SAA and a determination of the acetabular cup's spatial position and angular relationship to the pelvis. Further, the methods of the disclosure utilize the parameters of Bodner's Triangle, including the previously unrecognized angle referred to as the Pelvic Acetabular Angle PAA, in two new relationships to improve biomechanical position between the acetabular cup and pelvic position and mobility.

For example, the first relationship is SAA+PAA=PI+90. This is analogous to SS+PT=PI, but includes measurements related to the position of the acetabular cup. Experimental results have shown that when pelvic motion measured (dSS) is 25 degrees then SAA=PAA and Bodner's Triangle is an isosceles triangle. This relationship geometrically links the acetabular cup to a known dSS. In prior work, a sagittal relationship for dSS to cup position and mobility has been determined using Stefl et al data for mean and ranges for AI and SAA, which confirmed this new relationship was nearly identical to past clinical data calculations and revealed the exact ratios between parameters. As such, for any PI value when dSS is 25 degrees, the SAA=(PI+90)/2 and also equals SS+AI, which works at any dSS. This triangular relationship also dictates that, similar to positional parameters in the other relationships, SAA and PAA are reciprocal. If SAA changes in one direction, PAA must change the same amount in the other direction as the apex angle 90-PI never changes and the 3 angles of a triangle add to 180 degrees. So PAA at dSS of 25 degrees=SAA=(PI+90)/2 as well as the definition for any dSS, (90-AI)+PT.

The geometric effects were determined when this triangle moved in space over differing mobility dSS. The effect of changing SS and PT that define the pelvic position from the norm given by the 3:2:1 gear ratio of the pelvic construction was also determined. These master ratios became (3:2:1:−0.5:1.5)/(1.5:0.5) for (PI:SS:PT:AI:SAA)/(PAA:dSS). This means that when two normal patients present one with a PI of 54 and a second with a PI of 60, the first patient's numbers will be SS 41, PT 13, AI 31, SAA 72, and the second patient's numbers will be SS 45, PT 15, AI 30, SAA 75. However, they move in differing directions, when SS decreases and PT increases, AI increases but SAA decreases, when SS increases and PT decreases, AI decreases and SAA increases. The mobility ratio, that is, when a patient's measured dSS is not 25 degrees but rather any other number, for every degree divergent from 25 both the AI stand and the SAA change 0.5 degrees in the opposite direction, stiffness raising AI stand and SAA while lowering AI sit and PAA. For example, when dSS is 20 degrees, SAA goes up 2.5 degrees, AI goes up 2.5 degrees, PAA goes down 2.5 degrees. If dSS goes to 10 degrees, SAA and AI stand each go up 7.5 degrees, while AI sit and PAA each goes down 7.5 degrees. The inherent relationship of the acetabular cup to the pelvic position and to the mobility of the pelvis are all linear relationships that are leveraged by the methods of the present disclosure to tailor the acetabular cup position. The AI is the only parameter surgically determined in the whole system to either match the pelvis or to safely diverge from the pelvic machinery using the clinical limits defined in Stefl's work.

From the foregoing, a second relationship is observed such that when dSS=25 degrees and SAA and PAA each=(90+PI)/2, then for SAA=(90+PI)/2=AI+SS, and for PAA=(90+PI)/2=(90-AI)+PT. In addition, PAA+(AI-PT)=90 or 90-(AI-PT)=PAA. Known normative data for PI:SS:PT at dSS 25 degrees can then be utilized to create "master values" for the acetabular cup AI and SAA that look like this: PI 60, SS 45, PT 15, AI stand/sit 30/55, SAA/PAA 75, (AI-PT) 15. For PI 45, SS 35, PT 10, AI stand/sit 32.5/57.5, SAA/PAA 67.5, (AI-PT) 22.5. This can be done for any presenting PI. The last parameter, (AI-PT) is the positional and mobility dependent quotient that is utilized in the derived relationship; PI+(AI-PT)=SAA, which is defined as the unifying governing relationship bridging the acetabular and pelvic parameters. (AI-PT) changes by the same ratio as SAA/PAA, that is, when PI increases by 3°, (AI-PT) decreases by 1.5°, the same as PAA and reciprocally to SAA in any cup calculation. Both solutions, Bodner's triangle using presenting standing SS data with a single mobility correction and the AI-PT relationship requiring two corrections, one from normative pelvic position and the second for alteration in dSS mobility from 25 degrees to arrive at the geometrically optimal cup AI, SAA, and PAA, may be employed. The following methods of the present disclosure leverage biomechanical behavior of the pelvis and the acetabular cup in the lateral plane permitting determination of sagittal plane coordinates for a given patient's acetabular cup and also permit a determination of when the acetabular cup should not be placed in concert with aberrant spinopelvic behavior. For example, disease and degeneration within the spine-pelvis-hip system may not be compatible with known methods for acetabular cup placement. Compensatory mechanisms are involuntarily used by the body to keep gravity balanced standing and allow sitting to occur. These mechanisms may lead the pelvis to an unfavorable spatial position and/or aberrant mobility between postures that are beyond a safe position for the acetabular cup implant. The methods of the present disclosure include adjusted cup positions for such mechanical situations in the sagittal plane. The resulting positional-(tilt), and mobility-derived coordinates may be used (i) to advise or guide surgeons in selection of the location and orientation for the acetabular cup placement, (ii) to track these parameters in space for surgeons in real-time, (iii) to perform biplanar conversion to the coronal plane that surgeons inherently understand, and (iv) link these coordinates to robotic execution devices to navigate the acetabular cup.

EXAMPLE METHODS

In a pre-operative patient evaluation, X-rays are obtained to observe standing and seated lateral views from the L1 lumbar vertebra to the upper fifth of the femur, a standing anteroposterior ("AP") pelvis view, both an AP and lateral view of the hip and a modified Budin view for estimation of femoral stem version. In addition to or alternatively, transverse CT scans or MRI images may be obtained to observe one or more of these views. The patient is also evaluated to assess hip range of motion, including flexion, extension, contractures, internal rotation and external rotation. Biomechanical values from measurements derived from these X-rays include pelvic incidence (PI), sacral slope (SS), pelvic tilt (PT), delta (dSS) of the sacral slope (SS), pelvic femoral angle (PFA), leg length, hip offset and center of rotation, and femoral version.

Referring now to FIG. 10, a method 300 is illustrated using the preoperative templating apparatus 105 or navigation device 110 and computing device of FIGS. 1-2. Method 300 includes, at block 305, a processor determining a sagittal acetabular cup position in the form of a standing Anteinclination (AI), a seated AI and a SacroAcetabular Angle (SAA) based on at least one of (i) a standing sacral slope (SS) of a first patient relative to a normative SS, (ii) a delta of the sacral slope (dSS) of the first patient between a standing position of the first patient and an upright seated position of the first patient, (iii) a femoral version of the first patient, when the femoral version corresponds to a femoral version outlier position, and (iv) a pelvic femoral angle (PFA) of the first patient that corresponds to a PFA outlier position in at least one of a standing position, an upright seated position, or a delta between the standing position and the upright seated position. Then, at block 310, the processor determines a coronal acetabular cup position in the form of a supine coronal anteversion and at least one of a supine or a standing coronal inclination and anteversion based on the sagittal acetabular cup position. Next, at block 315, the processor determines a post-operative standing AI and a post-operative seated AI based on at least the coronal acetabular cup position.

The post-operative standing AI and the post-operative seated AI determined using the methods of the present disclosure may be utilized to manually place the acetabular cup in the first patient. For example, a surgeon may prepare and place the acetabular cup and stem with a handheld device and confirm the acetabular cup position based on computer feedback. Alternatively, robotics may utilize the post-operative standing AI and the post-operative seated AI for placement of the acetabular cup. For example, a navigation device with a tracking sensor may be linked to a mechanical arm that moves based on a pre-planned trajectory and desired coronal or sagittal position of the acetabular cup. The post-operative standing AI and the post-operative seated AI, once converted to coronal anteversion could also be used for acetabular and femur preparation, by inclusion of femoral considerations for planning appropriate combined anteversion and mobility.

In one optional embodiment, the method 300 includes the processor sending at least one of the sagittal acetabular cup position and the coronal acetabular cup position to a remote processor electrically coupled to at least one of a preoperative templating apparatus or a navigation device. In one embodiment, the processor is electrically coupled to at least one of a preoperative templating apparatus or a navigation device.

In another embodiment, the method 300 includes the processor receiving a plurality of biomechanical values including a pelvic incidence (PI), the sacral slope (SS), a pelvic tilt (PT), the delta of the sacral slope (dSS), the pelvic femoral angle (PFA), a leg length, a hip offset, a hip center of rotation, and the femoral version based on images of the first patient. In a further embodiment, the processor receiving the plurality of biomechanical values comprising the pelvic incidence (PI), the sacral slope (SS), the pelvic tilt (PT), the delta of the sacral slope (dSS), the pelvic femoral angle (PFA), the leg length, the hip offset, the hip center of rotation, and the femoral version based on the images of the first patient includes the processor receiving one or more digitized voice commands that include one or more of the plurality of biomechanical values. In another embodiment, the processor is electrically coupled to an audio-digital converter configured to digitize the one or more voice commands.

In an alternative embodiment, the method 300 includes the processor receiving the plurality of biomechanical values comprising the pelvic incidence (PI), the sacral slope (SS), the pelvic tilt (PT), the delta of the sacral slope (dSS), the pelvic femoral angle (PFA), the leg length, the hip offset, the hip center of rotation, and the femoral version based on the images of the first patient includes the processor receiving one or more signals from a user input module. And the one or more signals include one or more of the plurality of biomechanical values.

In another optional embodiment, the method 300 includes the processor determining or receiving a plurality of biomechanical values comprising a pelvic incidence (PI), the standing sacral slope (SS), a pelvic tilt (PT), the delta of the sacral slope (dSS), the pelvic femoral angle (PFA), a leg length, a hip offset, a hip center of rotation, and the femoral version based on one or more images including the first patient showing a standing lateral view from an L1 lumbar vertebra to an upper fifth of a femur, a seated lateral view from the L1 lumbar vertebra to the upper fifth of the femur, a standing anteroposterior (AP) pelvis view, an AP view of a hip, a lateral view of the hip and a modified Budin view.

In still another optional embodiment, the method 300 includes providing, via at least one of a display or an audio-digital converter, intraoperative guidance or control of a navigation device based on at least one of the sagittal acetabular cup position and the coronal acetabular cup position. In a further embodiment, determining the post-operative standing AI and the post-operative seated AI based on at least the coronal acetabular cup position includes the processor tracking anatomy of the first patient and the acetabular cup in real-time. And a plurality of sensors are coupled to one or more of the acetabular cup, the anatomy of the first patient and the navigation device and the plurality of sensors are electrically coupled to the processor. In another optional embodiment, the audio-digital converter is configured to permit two-way communication between a surgeon and the processor.

In another embodiment, the method 300 includes the display providing images showing a spatial position and an orientation of the acetabular cup in real-time. In a further embodiment, the method includes the processor determining an orientation of a femoral component.

In still another optional embodiment, the method 300 includes the processor registering anatomy of the first patient to an OR table. In a further embodiment, the processor synchronizes the registered anatomy of the first patient to a treatment path of a robotic arm of a navigation device and to at least one of the sagittal acetabular cup position and the coronal acetabular cup position.

In another embodiment, the method 300 includes a localization device confirming a plurality of placement parameters in a plurality of planes after implanting an acetabular cup in the first patient. In a further embodiment, the method 300 includes a localization device measuring changes in a post-operative state relative to a pre-operative state after implanting an acetabular cup in the first patient.

In yet another embodiment, the method 300 includes the processor determining at least one recommendation for a type of implant, a treatment plan or a surgical tip based on historical data from a plurality of patients. The historical data includes a plurality of coronal acetabular cup positions, a plurality of coronal or sagittal biomechanical values and measured changes in a post-operative state relative to a pre-operative state. The method also includes at least one of a display or audio-digital converter providing the at least one determined recommendation to a surgeon.

In one optional embodiment, the method includes the processor storing data associated with the first patient. The data includes the coronal acetabular cup position, a plurality of coronal or sagittal biomechanical values and measured changes in a post-operative state relative to a pre-operative state.

As discussed above, a non-transitory computer-readable medium having stored thereon program instructions that upon execution by a processor may be used to cause performance of any of the functions of the foregoing methods of the present disclosure.

As one example, a non-transitory computer-readable medium having stored thereon program instructions that upon execution by a processor, cause performance of methods that include the processor determining a sagittal acetabular cup position in the form of a standing Anteinclination (AI), a seated AI and a SacroAcetabular Angle (SAA) based on at least one of (i) a standing sacral slope (SS) of a first patient relative to a normative SS, (ii) a delta of the sacral slope (dSS) of the first patient between a standing position of the first patient and an upright seated position of the first patient, (iii) a femoral version of the first patient, when the femoral version corresponds to a femoral version outlier position, and (iv) a pelvic femoral angle (PFA) of the first patient that corresponds to a PFA outlier position in at least one of the standing position, the upright seated position, or a delta between the standing position and the upright seated position. The processor then determines a coronal acetabular cup position in the form of a supine coronal anteversion and at least one of a supine or a standing coronal inclination based on the sagittal acetabular cup position. Next, the processor determines a post-operative standing AI and a post-operative seated AI based on at least the coronal acetabular cup position.

Example 1

A 57 year old male with a height of 5'5" and a weight of 170 lbs presents with an arthritic L hip. The patient has normal motion with a small flexion joint contracture. His X-ray data are as follows; pelvic incidence PI is 54, stand/sit Sacral Slope SS is 27/9 such that his dSS is 18 degrees, stand/sit PFA is 200/139 such that his dPFA is 61, Lumbar stand/sit lordosis is 43/21 such that dLL is 22. In this example, a preoperative X-ray evaluation of his femoral anteversion is not available. Note that in alternative scenarios, transverse CT scans or Mill imaging may be used to obtain sagittal and/or coronal data. Lumbar lordosis and dLL are used to evaluate spinal stiffness but are not ultimately utilized to determine acetabular cup position.

To determine acetabular cup position in the sagittal plane, example methods of the present disclosure determine three values. The first determination is the normal cup position or architectural cup position for any patient with a pelvic incidence PI of 54. The second determination is the pelvic tilt PT adjustment (i.e., the adjustment for the standing deviation of this patient from that of the standing norm). The third determination is the dSS (i.e., the adjustment to that cup position based on the patient's pelvic mobility value).

The methods to derive these values are described in the disclosure above. In addition, the relationships PI=SS+PT and SAA=SS+AI can be rewritten as PI+(AI−PT)=SAA, where pelvic incidence PI and sacroacetabular angle SAA are constant values. Pelvic tilt PT adjustment and pelvic mobility dSS adjustment determine values for AI (and thus SAA). For any given patient, the measured pelvic incidence PI is fixed, but at the time of surgical presentation the pelvic tilt PT value may or may not be significantly different from the normative pelvic tilt PT value associated with that pelvic incidence PI. To determine a patient's anteinclination AI based on the foregoing relationships, a determination of the patient's SS or PT relative to the normative value for their pelvic incidence PI must be made to arrive at the tilt adjusted anteinclination AI (and SAA value). Then the tilt adjusted anteinclination AI must be further adjusted to account for the mobility difference dSS from the normative 25 degrees. For every degree the pelvic tilt PT diverges from the normative pelvic tilt PT value, the anteinclination AI is adjusted 0.25 degrees in the same positive or negative direction. Thus, if PT increases, then AI increases and vice versa. The resulting adjusted anteinclination AI is then adjusted a second time to account for the difference in mobility from 25 degrees, such that AI is increased 0.5 degrees for every degree of dSS divergence less than the normative 25 degrees and decreased 0.5 degrees for every degree of dSS divergence greater than 25 degrees. Using this twice adjusted AI and subtracting PT and then adding PI will result in the SAA value to determine optimal mechanical acetabular cup position.

The methods of the present disclosure were used to determine the architectural relationships between pelvic incidence PI, sacral slope SS, and pelvic tilt PT. For example, a ratio was determined such that starting at the PT intercept or 0-point, and pelvic incidence PI at 15 degrees, every 3 degree rise in pelvic incidence PI creates a 2 degree rise in sacral slope SS and 1 degree rise in pelvic tilt PT. In another example, for every 10 degree rise in pelvic incidence PI, sacral slope SS rises 6.67 degrees and pelvic tilt PT rises 3.33 degrees, a 3:2:1 ratio for PI:SS:PT. This determination permits a normative value to be determined for a given patient's pelvic incidence PI. These relationships are SS=5+0.666PI and PT=−5+0.333PI.

Figure 11:
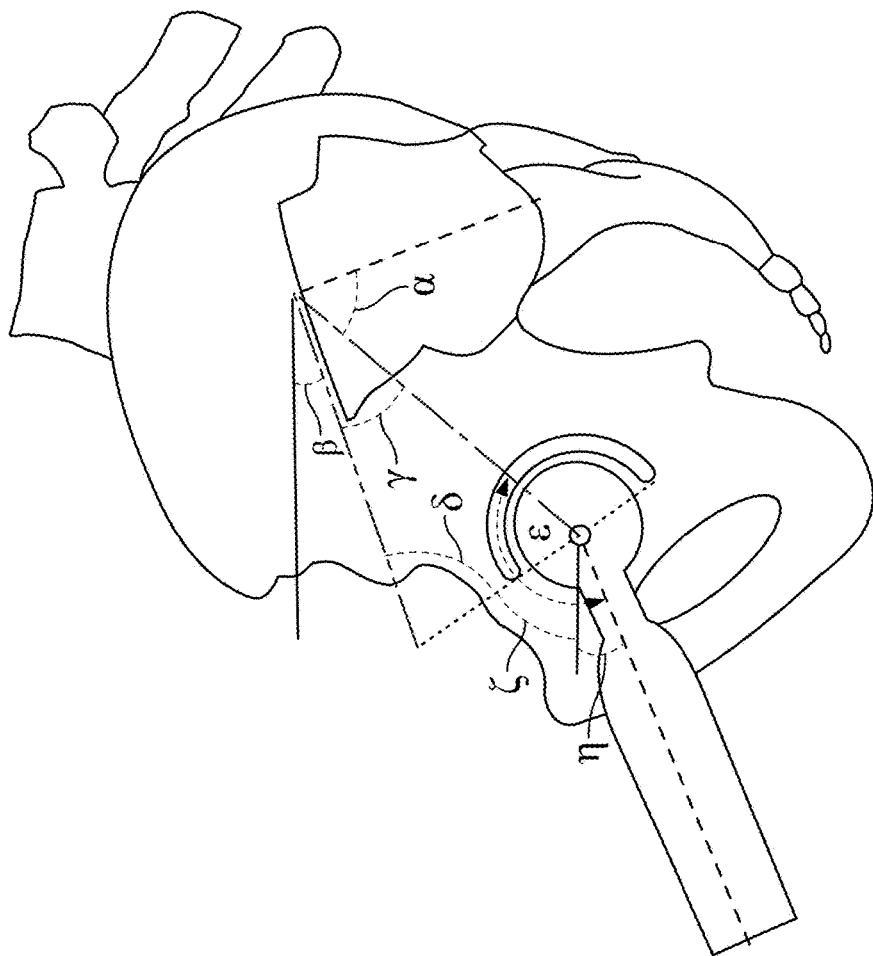
FIG. 11 shows a seated lateral view of the pelvis of FIG. 10 in which PI is 60° (α), SS is 20° (β), 90-PI is 30° (γ), SAA is 75° (δ), PAA is 75° (ε), AI is 55° (ζ), and PFA is 145° (η). In this position, Bodner's triangle rotates with the fulcrum on the hip joint, and the extent of the rotation is determined by delta SS (delta SS is 25° here). This opens the acetabulum 25° when sitting (1:1 ratio of delta SS:delta AI). Femoral motion (η) in this example is 50, as shown by the delta in PFA. The hip drives the rotation of Bodner's triangle back (ie, clockwise), tilting the pelvis posteriorly when sitting.

In addition, the mean pelvic incidence PI is typically considered to be about 53 degrees that corresponds to a sacral slope SS of about 40 degrees and a pelvic tilt PT of 13 degrees. Utilizing the ratio determined using the methods of the present disclosure, a pelvic incidence PI of 53 degrees has a sacral slope SS of 40.33 degrees and pelvic tilt PT of 12.67 degrees. The result is a table of normative values for pelvic incidence PI, sacral slope SS and pelvic tilt PT based on this 3:2:1 ratio provided in FIG. 11. PI appears to describe a sinusoidal rise over run relationship between the distance between the center of the hip and the center of S1, where the hypotenuse of a constructed right triangle may be described as 1/tan(90-PT). As PI increases the ratio of horizontal offset between hip and sacral centers increases with respect to the vertical distance between the two points. These physical changes all occur to provide a fixed ratio 3:2:1 between PI, SS, and PT such that for every 3 degrees PI changes, the SS angle changes 2 degrees and the PT changes 1 degree. With a 0 intercept for PT at 15 degrees of PI and SS, a determination can be made for absolute geometric normative values for any pelvis, the ratio of SS/PT giving a relative postural efficiency ratio between differing PI angles.

The methods of the present disclosure were then used to determine how this ratio impacted placement of an implanted acetabular cup whose sagittal values are known as AI and SAA. Specifically, Bodner's triangle permits this determination.

For example, the correlation between the position of the pelvis and hip are reflected by the relationships: PI=PT+SS and SS+AI=SAA. These two relationships share a common value, namely sacral slope SS. In addition, sacroacetabular angle SAA ties the position of the acetabular cup to the pelvis. The present disclosure recognizes for the first time a Pelvic Acetabular Angle PAA that creates a new relationship between the position of the acetabular cup and the pelvis to create Bodner's triangle. Bodner's triangle has three angles that correspond to the sacroacetabular angle SAA, the pelvic acetabular angle PAA and at the sacral apex ninety degrees minus pelvic incidence (90-PI). The angles of Bodner's triangle tie the position of the acetabular cup to sacral slope SS, to pelvic tilt PT, and to pelvic incidence PI. The anteinclination AI describes an angle with one limb measuring above the horizontal reference line, this same line is shared with both the sacroacetabular angle SAA and pelvic acetabular angle PAA. These lines are spatially identical and all three lines are created by the surgeon at the moment of acetabular cup placement (i.e., impaction) into the acetabulum of the pelvis. Once the sacroacetabular angle SAA and pelvic acetabular angle PAA are established, they become fixed constants and do not change. Only the anteinclination AI changes by the same number of degrees that the pelvis rotates between positions, the same amount as pelvis tilt, PT, and reciprocally to the SS amount, 1:1 ratios. As such, the position of the acetabular cup is correlated to the position of the hip via the relationship demonstrated in Bodner's triangle.

There is a condition in which Bodner's triangle becomes an isosceles, meaning that SAA=PAA. As this triangle consists of 3 constants, this means that these values will remain the same in both the standing and seated positions for a given patient. Bodner's triangle assumes this isosceles form when dSS is 25 degrees, and sacroacetabular angle SAA, which always is equal to SS+AI, becomes equal to (PI+90)/2. By substituting (PI+90)/2 for SS+AI, the result is that AI is the only remaining value to determine. This determination may be made based on pelvic incidence PI values for any sacral slope SS associated with pelvic incidence PI, which will provide the sacroacetabular angle SAA and therefore anteinclination AI.

Turning to the patient in the present example, the patient has a pelvic incidence PI of 54 degrees. As a result, in a healthy scenario the patient would typically have a sacral slope SS of 41 degrees and a pelvic tilt PT of 13 degrees. Then assuming he had 25 degrees of mobility, his sacroacetabular angle SAA would be (54+90)/2=72 making his standing anteinclination AI 72-41=31. And if the patient had a dSS of 25 degrees, his seated anteinclination AI would be 31+25=56. The foregoing would be the standard baseline values for the patient.

However, the patient presented with a sacral slope of 27 degrees, rather than 41 degrees, and his dSS is 18 degrees, not 25 degrees. In order to determine the acetabular cup angle in view of the present sacral slope SS and to permit 25 degrees of pelvic mobility, the ratio for PI:SS:PT determined by the methods of the present disclosure may be used. Here, a pelvic incidence PI of 33 degrees has a norm sacral slope SS of 27 degrees, a sacroacetabular angle SAA of 61.5 degrees and anteinclination AI of 34.5 degrees. The standing sacral slope SS provides a tilt adjusted standing anteinclination AI, regardless of the pelvic incidence PI, here 34.5 degrees.

Bodner's triangle, once established via acetabular cup placement (i.e., impaction), moves in space between the standing and seated positions, and the acetabular cup moves exactly the same angular amount and direction. However, the amount of pelvic mobility, as measured by dSS, has an effect on a determination of the preferred angle of the acetabular cup. A 25 degree change between the standing and seated positions does not require any alteration to the tilt adjusted acetabular cup position. But for every degree that dSS deviates from the normative 25 degrees of pelvic mobility both anteinclination AI and sacroacetabular angle SAA move 0.5 degrees. For example, when dSS is lower than 25 degrees, sacroacetabular angle SAA and anteinclination AI increase by 0.5, and when dSS is above 25 degrees, sacroacetabular angle SAA and anteinclination AI decrease by 0.5.

Taking into account the patient's pelvic mobility dSS of 18 degrees, 25−18=7, such that the patient is 7 degrees stiffer than the norm. Applying the methods of the present disclosure, the patient's anteinclination AI and sacroacetabular angle SAA are increased 3.5 degrees. Further, based on the patient's actual measured values as presented above, his final mechanical acetabular cup position is based upon 34.5+3.5=38 standing anteinclination AI and his seated anteinclination AI is 38+18=56. His sacroacetabular angle SAA value is determined to be 61.5+3.5=65. Thus, for every degree that sacral slope SS decreases or pelvic tilt PT increases from the pelvic incidence PI normative value, the anteinclination AI increases 0.25 degrees and sacroacetabular angle SAA decreases 0.75 degrees. The change in the sacroacetabular angle SAA is determined by PI+(AI−PT)=SAA. And parameter (AI−PT) will decrease 0.75 degrees even as anteinclination AI goes up 0.25 degrees, because pelvic tilt PT is subtracted and PT moves in the same direction as the anteinclination AI moves. Once again, when the pelvis rolls back 1 degree, the pelvic tilt PT will increase 1 degree from the normative value, the anteinclination AI (i.e., the acetabular cup anteversion) increases 0.25 degrees and the parameter (AI−PT) becomes (0.25−1)=−0.75 which reflects the change to the sacroacetabular angle SAA value.

Based on the foregoing, the patient has a mechanical plan for placement of his acetabular cup, with a sacroacetabular angle SAA of 65 degrees and stand/sit anteinclination AI 38/56. Most patients do not change their standing sacral slope SS postoperatively. As such, the approach during surgery is to place an acetabular cup using lateral plane fluoroscopy guidance creating an sacroacetabular angle SAA of 65 degrees on the OR table. The patient's coronal values are then determined in order to use fluoroscopic control to view coronal inclination that is measured as an angle. The methods of the present disclosure are used to target the acetabular cup's anteversion based on the sacroacetabular angle SAA and the coronal inclination by converting sagittal values to coronal values.

The sagittal-to-coronal conversion is conducted by superimposing the sagittal coordinates over mobility-dependent coronal coordinates published by Dr. Dorr. Depending on the patient, these mobility-dependent coronal coordinates are in the form of a 10×10 degree window for normal mobility, a 5×5 degree window for stiff mobility and a 5×8 degree window for hypermobility. This conversion accounts for 35-50 degrees of coronal inclination and 12-25 degrees of anteversion. The conversion exceeded 25 degrees supine anteversion to account for cases of very stiff, very high pelvic incidence PI and high standing sacral slope SS such that coronal anteversion will need to go closer to 30 degrees. The angle at which the sagittal coordinates are overlaid relative to the coronal plane will have some effect on the conversion angle, but a reasonable estimation of this value may be utilized. Machine learning methods of the present disclosure permits a processor in the system to learn from acetabular cup placement outcomes to improve the sagittal-to-coronal conversion over time. The methods of the present disclosure have been clinically confirmed with about 50 procedures.

With the sagittal conversion values, anteversion AI can be determined a priori without resort to Bodner's triangle thereby providing an optimal sacroacetabular angle SAA value. For example, the relationship PI+(AI−PT)=SAA can be used based on the pelvis mobility dSS value from the sagittal values determined and measured above. With respect to the patient of the present example, his pelvic incidence PI is 54 degrees and his measured PT is 14 degrees more than his normative PT value. His tilt adjusted anteinclination AI adds 0.25×14=3.5 degrees to his normative anteinclination AI value of 31 degrees resulting in a final tilt adjusted AI of 31+3.5=34.5 degrees. And his pelvic mobility adjustment to both AI and SAA is 0.5×(25−18)=3.5 giving a final standing anteinclination AI of 34.5+3.5=38 and SAA of 38+27 (his measured preoperative standing SS)=65. The foregoing values are based on conversion ratios, rather than Bodner's triangle, as an alternative implementation of the methods of the present disclosure.

Turning to Bodner's triangle, SAA−(AI−PT)=PI and the complement is PAA+(AI−PT)=90. The same conversion ratios disclosed above can be used to determine anteinclination AI and pelvic acetabular angle PAA. In addition, the sacroacetabular angle SAA can be determined by (90+PI)−PAA=SAA.

In view of the foregoing, there are six parameters to consider when determining the normative values based on pelvic incidence PI, and then adjusted to determine individual acetabular cup position when the patient's pelvic position and mobility have deviated from architectural values in standing to sitting. The first set is the morphologic ratios as PI changes from one value to another, these ratios are PI: SS:PT:AI: SAA=3:2:1:0.5:1.5, with the sixth parameter the dSS mobility correction of 0.5 With the above ratios a complete set of normative values may be tabulated. When an individual patient presents with altered values for hip replacement, tilt adjusted cup position may be determined from the normative data by these individual conversion ratios, SS:PT:AI:SAA:dSS=1:1:0.25:0.75:0.5. The former set may be used to illustrate the change in cup values between patients when pelvic incidence PI increases by 1 degree, then PI(+1)+[AI(−0.17)−PT(0.33)]=SAA or 1+(−0.5)=+0.5 which means as pelvic incidence PI increases by one degree, the quotient (AI−PT) decreases 0.5 degrees resulting in a sacroacetabular angle SAA increase of 0.5 degrees, namely the effect of a change to pelvic incidence PI on acetabular cup position and sacroacetabular angle SAA. For an individual patient with a fixed pelvic incidence PI and changing sacral slope SS and pelvic tilt PT, the same relationship has a different solution, it becomes PI(+0)+[AI(0.25)−PT(1)]=SAA. In other words, for each degree pelvic tilt PT increases, anteinclination AI increases 0.25 degrees and sacroacetabular angle SAA decreases 0.75 degrees. This represents the tilt adjustment ratios before the 0.5 degree mobility correction (that is, deviation from the 25 degree norm) is applied to the anteinclination AI and sacroacetabular angle SAA values.

The overall spinopelvic balance of the hip replacement's acetabular cup position can be described by the relationship of the sacroacetabular angle SAA to the pelvic acetabular angle PAA, SAA:PAA. When the relationship of the acetabular cup to both the SS (SAA) and the PT (PAA) is equal the system is balanced. That is SAA=PAA and that occurs when SAA and PAA are both equal to (PI+90)/2. A perfectly balanced system is not always achievable for a given patient and the best possible outcome may be skewed towards the SAA where a patient has stiff mobility or a persistent rotated-forward pelvic position. For the typical Caucasian patient with a pelvic incidence PI of 54 degrees, the balanced SAA and PAA are both 72 degrees, i.e., (54+90)/2. Therefore 72:72 describes a balanced SAA:PAA ratio (a harmonious spinopelvic balance) for a hip replacement in a normal patient with a pelvic incidence PI of 54. From the previous ratios, this occurs when dSS=25 degrees or when the effect of an alteration in pelvic position is countered by an alteration due to mobility. Stiffness is countered by decreased sacral slope SS, whereas increased dSS mobility is countered by an increased sacral slope SS. The clinically normal pelvic mobility in patients presenting for THA is 20 degrees stand to sit such that the SAA:PAA ratio for a typical patient with a PI of 54 and 20 degrees mobility become 74.5:69.5. These are the values for SAA and PAA derived from relationships and determinations based on Bodner's triangle, when the pelvic incidence PI is 54 and the dSS is 20. The patient in the present example with a pelvic incidence PI of 54 has a SAA:PAA ratio of 65:79. As such, he is significantly off the balanced SAA:PAA ratio of 72/72, because he is stiffer but there is a much greater effect from his lowered standing sacral slope SS that effectively decreases the SAA and increases the PAA.

In summary, conditions that increase SAA and lower PAA are decreasing dSS mobility (pelvic stiffness, and increasing pelvic tilt position forward (i.e., raising sacral slope SS and decreasing pelvic tilt PT). Conditions that lower SAA and increase PAA are increasing dSS mobility and increasing pelvic spatial position backward (i.e., decreasing sacral slope SS and increasing pelvic tilt PT). Conditions that increase both SAA and PAA thereby increase pelvic incidence PI, whereas conditions that lower both SAA and PAA thereby decrease pelvic incidence PI. In other words, the sacroacetabular angle SAA increases and pelvic acetabular angle PAA decreases, when pelvic mobility decreases and the pelvis tilts forward. The sacroacetabular angle SAA decreases and pelvic acetabular angle PAA increases, when pelvic mobility increases and the pelvis tilts backwards.

The patient in the present example has a compromised standing posture. Specifically, his pelvis is significantly tilted (rotated) posteriorly driving his sacroacetabular angle SAA down. But the decreased pelvic mobility, which raises the sacroacetabular angle SAA, does not compensate enough to restore absolute balance where SAA=PAA. As a result, his optimal acetabular cup position is skewed to the pelvic tilt PT side, the PAA side that is higher than his sacral slope side, the SAA side. As a result, the SAA:PAA ratio permits determination of an acetabular cup's spatial relationship relative to the individual patient's deteriorating hip and spine alignment.

Next, the relationship of the acetabular cup's position to the femur is determined to satisfy the parameter known as combined anteversion. The coronal cup anteversion is accepted as measured by an ellipse methodology on the AP X-ray and adding the same to the femoral anteversion as estimated visually at the time of surgery or by matching the femur to a preoperative CT scan and using navigation to arrive at a number. Femoral version is based on the relationship of the position of the center of the head of the femoral component to the longitudinal axis of the femur, an angle is determined from the posterior condylar line of the knee (essentially creating an internal horizontal reference line) and the deviation of the neck of the femoral component to this reference line. This angle is added to the acetabular cup's coronal anteversion to achieve a 25-45 degree range between the femoral version and the cup's coronal version (typically men range from 25-37 and women range from 30-45). The femoral version typically ranges from 7-20 and typically the cup coronal anteversion range is from 15-25. If femoral version is below 5 degrees or above 25 degrees, the femoral version is best changed, which is difficult with the preferred uncemented press fit femoral components. The intraoperative result is that surgeons who use combined anteversion as a guide may elect to modify acetabular cup version from the mechanical plan described above and permit the femoral stem implant find its unaltered seating.

A second correction may be applied to outlier femoral mobility, a measure different from femoral cup version. This is measured as another sagittal parameter as the femur moves in the sagittal plane. The value is Pelvic Femoral Angle (PFA) by Dorr and Sacro Femoral Angle (SFA) by spine surgeons. Outliers are typically associated with; 1) stiffness of the pelvis as PFA has been found to increase 0.9 degrees for every degree loss of dSS leading to an increased delta PFA and 2) elevated PT standing, associated with a high standing PFA and a low sitting PT, associated with a low sitting PFA. The sagittal parameter defined as predicting functional safe cup placement is called Combined Sagittal Index (CSI) and is measured as the sum of AI+PFA=CSI. CSI is a position and PI-dependent value. The CSI has both standing and sitting values ranging between an upper limit to avoid a high standing CSI value that could result in an anterior dislocation and a lower limit to avoid a low sitting CSI value that could result in a posterior dislocation. Low pelvic incidence PI patients are particularly prone to a low sitting CSI value. To account for this, the methods of the present disclosure, adjust anteinclination AI upwards on a sliding scale, depending on how low the PFA is below the 120 degree normal value. Likewise, if a patient is above 197 standing CSI value, the methods of the present disclosure, adjust the anteinclination AI downward on a sliding scale. This adjustment is optional, but not required, for acetabular cup placement. PFA outliers are associated with stiffness frequently and the targeting corrections for stiffness can solve most of the issues. Insuring a proper or increased coronal offset and leg length resolves the rest.

Finally, values corresponding to the determined acetabular cup values may be further modified based on the natural anatomical depth and version of the patient's acetabulum. For example, a patient may present with a mismatch between the determined position for the acetabular cup and the depth of the cup that the acetabulum can accept without the cup extending out of the socket of the acetabulum.

In addition, in one optional embodiment, the relationships described herein, including the sagittal-to-coronal conversion will be provided in a tangible computer readable media with instructions for execution on one or more processors for a preoperative templating apparatus and/or an intraoperative navigation system. In toto, all this targeting information may then be confirmed in a computer simulation defining a "Range of Motion to Impingement" sequence using sagittal and coronal biplanar positions simultaneously.

Example 2

There is only one tilt-adjusted acetabular cup position for any presenting standing sacral slope SS regardless of the pelvic incidence PI. In other words, acetabular cup position is not dependent on the construction of the pelvis with regards to pelvic incidence PI. Instead, acetabular cup position depends on the presenting pelvic position as measure by sacral slope SS as described here or by pelvic tilt PT based on the relationship PAA+(AI−PT)=90. The result is that the patient from Example 1 above and the patient in the present Example 2 both have an acetabular cup positioned in the same orientation, but the balance between the acetabular cup and the pelvis as determined by the values of sacral slope SS and pelvic tilt PT in relation to their respective pelvic incidence PI will be different.

For example, a female that has a pelvic incidence PI of 45 degrees, when she was 20 years old, also has a standing sacral slope SS of 35 with a pelvic tilt PT of 10 degrees, which is a normal distribution. At age 65, the same female now has a standing sacral slope SS of 30 degrees and a pelvic tilt PT of 15 degrees, and her tilt adjusted intraoperative cup position will be based on her current sacral slope SS of 30. A second patient presents with a pelvic incidence PI of 35 degrees but also has a presenting standing sacral slope SS of 30 degrees and a pelvic tilt PT of 5 degrees. Both of these patient's tilt adjusted standing cup positions will be the same, since the cup position is based on their presenting standing sacral slope SS of 30 degrees. Both patients will have a tilt adjusted cup anteinclination AI of 33.75 degrees standing and their sacroacetabular angle SAA will be 63.75 degrees. When a patient's dSS is determined, an adjustment to this standing anteinclination AI position can be applied to determine the sitting anteinclination AI, and to similarly adjust the sacroacetabular angle SAA to arrive at the tilt & mobility-dependent mechanical acetabular-sided cup position. In this example if patient 1 has a dSS of 15 degrees, her AI standing is changed to 38.75 and sitting becomes 53.75 with an SAA of 68.75 if patient 2 has dSS of 35 degrees, her standing AI drops to 28.75 and sitting becomes 63.75 with an SAA of 58.75.

The description of different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

The invention claimed is:

1. A method, comprising:
determining, via a processor, a sagittal acetabular cup position in the form of a standing Anteinclination (AI), a seated AI and a SacroAcetabular Angle (SAA) based on at least one of (i) a standing sacral slope (SS) of a first patient relative to a normative SS, (ii) a delta of the sacral slope (dSS) of the first patient between a standing position of the first patient and an upright seated position of the first patient, (iii) a femoral version of the first patient, when the femoral version corresponds to a femoral version outlier position, and (iv) a pelvic femoral angle (PFA) of the first patient that corresponds to a PFA outlier position in at least one of the standing position, the upright seated position, or a delta between the standing position and the upright seated position;
determining, via the processor, a coronal acetabular cup position in the form of a supine coronal anteversion and at least one of a supine or a standing coronal inclination and anteversion based on the sagittal acetabular cup position; and
determining, via a processor, a post-operative standing AI and a post-operative seated AI based on at least the coronal acetabular cup position.

2. The method of claim 1, further comprising:
sending, via the processor, at least one of the sagittal acetabular cup position and the coronal acetabular cup position to a remote processor electrically coupled to at least one of a preoperative templating apparatus or a navigation device.

3. The method of claim 1, wherein the processor is electrically coupled to at least one of a preoperative templating apparatus or a navigation device.

4. The method of claim 1, further comprising:
receiving, via the processor, a plurality of biomechanical values comprising a pelvic incidence (PI), the sacral slope (SS), a pelvic tilt (PT), the delta of the sacral slope (dSS), the pelvic femoral angle (PFA), a leg length, a hip offset, a hip center of rotation, and the femoral version based on images of the first patient.

5. The method of claim 4, wherein receiving, via the processor, the plurality of biomechanical values comprising the pelvic incidence (PI), the sacral slope (SS), the pelvic tilt (PT), the delta of the sacral slope (dSS), the pelvic femoral angle (PFA), the leg length, the hip offset, the hip center of rotation, and the femoral version based on the images of the first patient comprises:
receiving, via the processor, one or more digitized voice commands that include one or more of the plurality of biomechanical values.

6. The method of claim 5, wherein the processor is electrically coupled to an audio-digital converter configured to digitize the one or more voice commands.

7. The method of claim 4, wherein receiving, via the processor, the plurality of biomechanical values comprising the pelvic incidence (PI), the sacral slope (SS), the pelvic tilt (PT), the delta of the sacral slope (dSS), the pelvic femoral angle (PFA), the leg length, the hip offset, the hip center of rotation, and the femoral version based on the images of the first patient comprises:
receiving, via the processor, one or more signals from a user input module, wherein the one or more signals include one or more of the plurality of biomechanical values.

8. The method of claim 1, further comprising:
determining or receiving, via the processor, a plurality of biomechanical values comprising a pelvic incidence (PI), the standing sacral slope (SS), a pelvic tilt (PT), the delta of the sacral slope (dSS), the pelvic femoral angle (PFA), a leg length, a hip offset, a hip center of rotation, and the femoral version based on one or more images comprising the first patient showing a standing lateral view from an L1 lumbar vertebra to an upper fifth of a femur, a seated lateral view from the L1 lumbar vertebra to the upper fifth of the femur, a standing anteroposterior (AP) pelvis view, an AP view of a hip, a lateral view of the hip and a modified Budin view.

9. The method of claim 1, wherein further comprising:
providing, via at least one of a display or an audio-digital converter, intraoperative guidance or control of a navigation device based on at least one of the sagittal acetabular cup position and the coronal acetabular cup position.

10. The method of claim 9, wherein determining the post-operative standing AI and the post-operative seated AI based on at least the coronal acetabular cup position comprises tracking, via the processor, anatomy of the first patient and the acetabular cup in real-time, wherein a plurality of sensors are coupled to one or more of the acetabular cup, the anatomy of the first patient and the navigation device and the plurality of sensors are electrically coupled to the processor.

11. The method of claim 9, wherein the audio-digital converter is configured to permit two-way communication between a surgeon and the processor.

12. The method of claim 9, further comprising:
providing, via the display, images showing a spatial position and an orientation of the acetabular cup in real-time.

13. The method of claim 12, further comprising:
determining, via the processor, an orientation of a femoral component.

14. The method of claim 1, further comprising:
registering, via the processor, anatomy of the first patient to an OR table.

15. The method of claim 14, further comprising:
synchronizing, via the processor, the registered anatomy of the first patient to a treatment path of a robotic arm of a navigation device and to at least one of the sagittal acetabular cup position and the coronal acetabular cup position.

16. The method of claim 1, further comprising:
after implanting an acetabular cup in the first patient, confirming, via a localization device, a plurality of placement parameters in a plurality of planes.

17. The method of claim 1, further comprising:
after implanting an acetabular cup in the first patient, measuring, via a localization device, changes in a post-operative state relative to a pre-operative state.

18. The method of claim 1, further comprising:
determining, via the processor, at least one recommendation for a type of implant, a treatment plan or a surgical tip based on historical data from a plurality of patients, wherein the historical data comprises a plurality of coronal acetabular cup positions, a plurality of coronal or sagittal biomechanical values and measured changes in a post-operative state relative to a pre-operative state; and providing the at least one determined recommendation, via at least one of a display or audio-digital converter, to a surgeon.

19. The method of claim 1, further comprising:

storing, via the processor, data associated with the first patient, the data comprising the coronal acetabular cup position, a plurality of coronal or sagittal biomechanical values and measured changes in a post-operative state relative to a pre-operative state.

20. A non-transitory computer-readable medium having stored thereon program instructions that upon execution by a processor, cause performance of a method comprising:

the processor determining a sagittal acetabular cup position in the form of a standing Anteinclination (AI), a seated AI and a SacroAcetabular Angle (SAA) based on at least one of (i) a standing sacral slope (SS) of a first patient relative to a normative SS, (ii) a delta of the sacral slope (dSS) of the first patient between a standing position of the first patient and an upright seated position of the first patient, (iii) a femoral version of the first patient, when the femoral version corresponds to a femoral version outlier position, and (iv) a pelvic femoral angle (PFA) of the first patient that corresponds to a PFA outlier position in at least one of the standing position, the upright seated position, or a delta between the standing position and the upright seated position;

the processor determining a coronal acetabular cup position in the form of a supine coronal anteversion and at least one of a supine or a standing coronal inclination and anteversion based on the sagittal acetabular cup position; and the processor determining a post-operative standing AI and a post-operative seated AI based on at least the coronal acetabular cup position.

* * * * *